(12) United States Patent
Kim et al.

(10) Patent No.: US 9,398,935 B2
(45) Date of Patent: Jul. 26, 2016

(54) ROBOTIC IMAGING SYSTEM

(71) Applicant: The Board of Trustees of the Leland Stanford Junior University, Palo Alto, CA (US)

(72) Inventors: Hyun Kim, Menlo Park, CA (US); Joan Savall, Palo Alto, CA (US); Jerome Anthony-Jean Lecoq, Menlo, CA (US); Mark Schnitzer, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 201 days.

(21) Appl. No.: 14/466,199

(22) Filed: Aug. 22, 2014

(65) Prior Publication Data

US 2015/0057550 A1    Feb. 26, 2015

Related U.S. Application Data

(60) Provisional application No. 61/868,668, filed on Aug. 22, 2013.

(51) Int. Cl.
*A61B 6/00* (2006.01)
*A61B 19/00* (2006.01)
*A61B 5/00* (2006.01)
*A61B 1/00* (2006.01)

(52) U.S. Cl.
CPC ........... *A61B 19/2203* (2013.01); *A61B 5/0042* (2013.01); *A61B 5/0062* (2013.01); *A61B 1/00163* (2013.01); *A61B 5/0071* (2013.01); *A61B 5/0082* (2013.01); *A61B 5/6868* (2013.01); *Y10S 901/47* (2013.01)

(58) Field of Classification Search
CPC ........... A61B 19/2203; A61B 1/00163; A61B 5/0042; A61B 5/0062; A61B 5/0071; A61B 5/0082; A61B 5/6868; Y10S 901/47
See application file for complete search history.

(56) References Cited

U.S. PATENT DOCUMENTS

2010/0168586 A1* 7/2010 Hillman ............ G02B 23/2476
600/476

* cited by examiner

*Primary Examiner* — Mark Remaly
(74) *Attorney, Agent, or Firm* — Kaplan Breyer Schwarz & Ottesen, LLP

(57) ABSTRACT

A robotic imaging system has at least one robotic imaging arm that includes a free-space optics subsystem. The free-space optics is capable of conveying an excitation light signal through the robotic imaging arm to an optical end effector at the distal end thereof while maintaining coaxial alignment between the optical axis and the robotic skeleton. The free-space optics is also capable of maintaining linear polarization of the light signal.

20 Claims, 5 Drawing Sheets

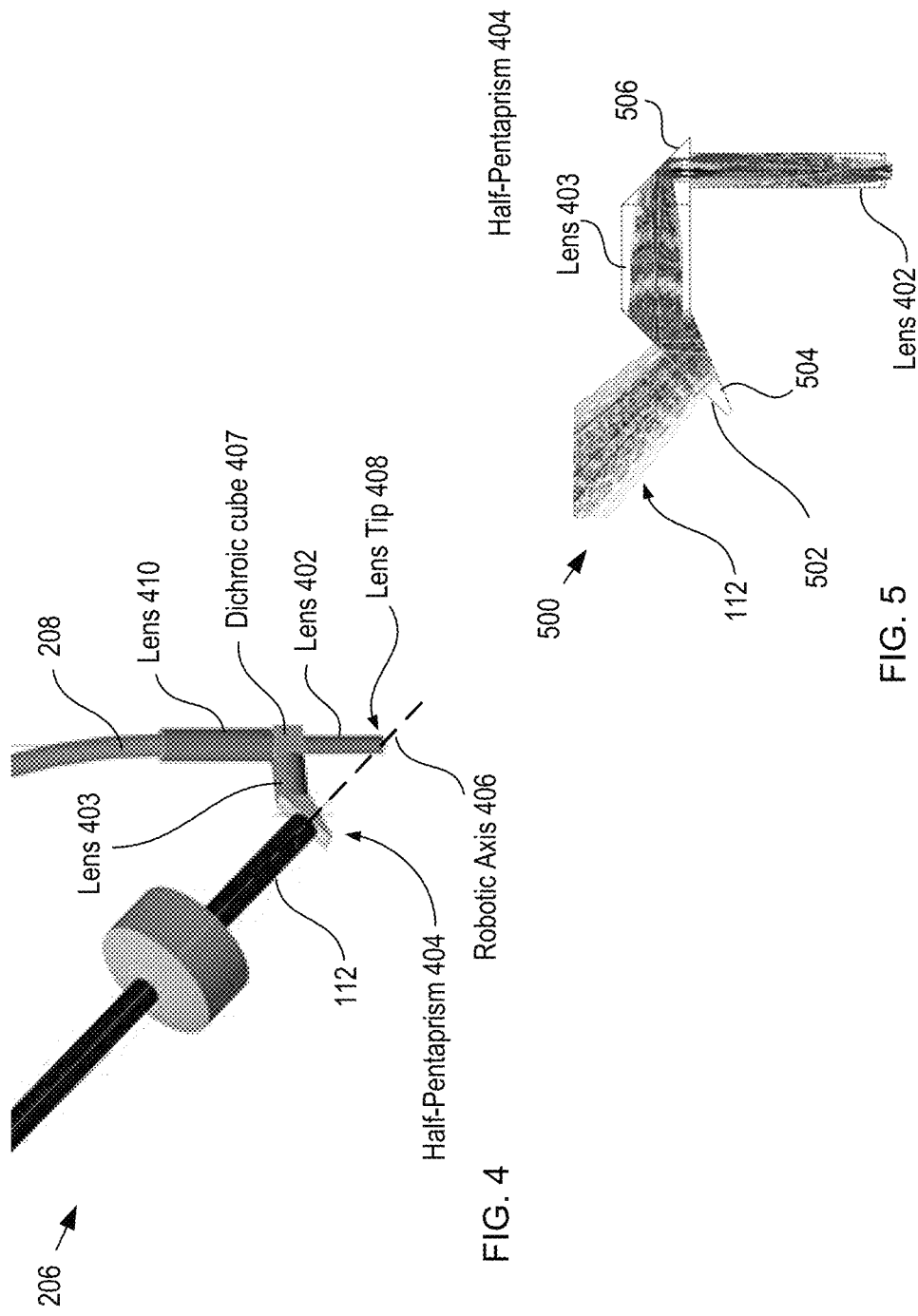

ROBOTIC IMAGING SYSTEM

STATEMENT OF RELATED CASES

This case claims priority of U.S. Pat. Application 61/868,665, which was filed on Aug. 22, 2013 and is incorporated herein by reference.

FIELD OF THE INVENTION

The present invention relates to microscopy in general, and, more particularly, to in-vivo microscopic imaging of the brain.

BACKGROUND OF THE INVENTION

Related interactions often occur at different regions of the brain and/or at different depths therein. The interrelationship of these interactions contains information that can provide insight into overall brain function, health, information processing, and the effects of pharmacological agents on the brain or other parts of the body. For example, in neuroscience, it is desirable to characterize the manner in which brain activity flows from one region to the next with cellular resolution. This is essential as information processing in the brain requires the collaborative and simultaneous work of multiple brain areas. In medicine, it is desirable to follow the simultaneous effect of new drugs on multiple parts of the body. Any pharmacological agent will have multiple and simultaneous effect on various parts of the body that need to be understood to fully appreciate its mode of action.

Consequently, in brain-imaging applications, it is often desirable to image disparate regions of the brain. Conventional microscopes are often employed for this service. A conventional microscope typically includes an imaging system that is upright and includes a large vertical objective, while offering three translational degrees of freedom for the relative positioning of the microscope and a sample.

Unfortunately, conventional microscopes are ill-suited for many brain imaging applications. First, the sample is normally constrained to lie flat on the microscope stage, while a brain is a three-dimensional object.

Second, the field-of-view of a conventional microscope is typically inversely proportional to the imaging resolution desired. As a result, high-resolution microscopy is normally limited to very small fields-of-view and is typically characterized by poor depth-of-field. As a result, it is difficult, if not impossible, to image different parts and/or depths of a brain at the same time. A conventional microscope, therefore, is incapable of providing information about coordinated brain activity at such scales.

Furthermore, using multiple microscopes to simultaneously image different regions of a brain is impractical due to the considerable bulk of a conventional microscope. This size constraint is particularly problematic when imaging small brains, such as a rodent or fly brain, as is commonly used in research.

In addition, the limited degrees-of-freedom of a typical microscope makes it illsuited for use during robotic brain surgery, which requires that an imaging system be carefully placed at any desired location and orientation with respect to a patient's brain.

As an alternative to conventional microscopes, light-based robotic therapy systems have been developed. Typically, the optical end effector is optically coupled to a light source via optical-fiber connections (e.g., through a catheter, etc.). Optically coupling the end effector and light source with an optical fiber limits the spectral bandwidth—among other light properties (e.g. polarization, pulse duration in case of ultrafast light sources)—available to the practitioner.

SUMMARY OF THE INVENTION

The present invention enables microscopic imaging at any point on a three-dimensional sample along an arbitrary direction. In some embodiments, the present invention enables simultaneous microscopic imaging at multiple locations and orientations.

An illustrative embodiment of the invention comprises a robotic two-photon microscopy imaging system. The robotic imaging system integrates an optical microscopy system with a robotic system having at least one robotic arm. The inventors recognized that if the optics of the microscopy system could be appropriately integrated in and adapted for use with a robotic system, the many translational and rotational degrees of freedom of the robotic system could provide an imaging system with essentially unfettered and unprecedented access to a three-dimensional sample.

As a consequence, embodiments of the present invention are particularly well suited for in-vivo brain imaging and simultaneous multi-area imaging of disparate brain subsystems. Furthermore, embodiments of the present invention can cooperatively interact with devices implanted in the brain, thus enabling simultaneous surface-image and deep-imaging of the brain. In some embodiments, embodiments of the present invention enable control of biological samples via optogenetic techniques (i.e., using light to control neurons that have been genetically sensitized to light).

In some embodiments, the robotic imaging system comprises a robotic system having two, three or more robotic arms, enabling simultaneous imaging at multiple sites of a sample.

The optics of the robotic imaging system deliver excitation light, through the robotic imaging arms, to an optical end effector that is disposed at the tip of each such arm. A free-space optical arrangement is used to deliver the excitation light to the objective (optical end effector). The elements of the free-space optical system are integrated within the body of each robotic arm. In the illustrative embodiment, the excitation light is laser light. In some embodiments, the optical system provides multiple light beams, each having different wavelengths (and/or other properties, such as polarization, spatial mode profile, etc.), to one or more regions of a sample to be imaged. The robotic imaging system is suitable for both single-photon and two-photon excitation microscopy.

A very important aspect of the illustrative embodiment is the miniaturization of the optical end effector of the imaging system. The inventors recognized that miniaturization of the optical end effector (i.e., the objective) would enable the robotic imaging system to make full and best use of (1) multiple robotic imaging arms and (2) the two rotational degrees of freedom possessed by the robotic arms. The miniaturized optical end effector used in some embodiments of the present invention has a final cross-sectional diameter of about 1 millimeter, which enables simultaneous placement of multiple robotic imaging arms around a single animal without collision.

By way of comparison, even sophisticated prior-art devices for multi-photon imaging that include one rotational degree-of-freedom (and three translational degrees-of-freedom), such as the "Bergamo II" by Thorlabs, Inc. or the "MOM" by Sutter Instrument, incorporate a commercially available microscope objective, such as the Olympus XLUMPLFLN. Microscope objectives, such the XLUMPLFLN or others suitable for this application, have a cross-sectional diameter of about 1 inch. In the context of brain investigation, where the typical subject is a mouse brain or brain of other small animals (e.g., small primates, etc.), 1 inch represents a significant bulk. An objective of this size would not permit the simultaneous investigation of multiple brain areas in a single animal because the multiple relatively large objectives would collide. Consistent with this, to the inventors' knowledge, no provider of such imaging microscopes claim an ability for simultaneous multiple-site imaging.

With respect to two-photon microscopy, the ability to deliver laser light through free space, as in embodiments of the invention, has an extremely important advantage relative to conventional microscopy. Given the current state of optical fiber technology, the use of an optical fiber to deliver the laser light to the optical end effector would limit a biologist, for example, to working with a specific wavelength and hence a specific biological marker. But there are no such limits using free space optics; the microscope can therefore be a wide-bandwidth device (i.e., many laser wavelengths can be used). This enables the biologist to access the wide variety of biological fluorescent markers responding at different wavelengths.

Since the excitation light is not delivered to the optical end effector by a fiber but rather by an arrangement of free-space optics disposed within the robotic arms, there is the challenge of ensuring that the optical axis of light passing through each arm remains co-aligned with the "skeleton" of the arm.

Furthermore, embodiments of the invention provide an optical end effector design that is compatible with robotic motion. Robotic designs used in the illustrative embodiments employ kinematics known as "remote center of motion" ("RCM"), wherein the end effector pivots about a remote point (i.e., a point that is distanced from the mechanical bulk of the robotic arm). The robotic arms are designed this way because RCM will facilitate access of multiple optical end effectors to small samples.

Since the robot kinematics define a unique point in space (the RCM), the optical system must be compatible with an RCM robotic arm. In embodiments of the invention, the axis of the excitation light coincides with the end of the final lens in the optical end effector. This ensures that the robot will pivot about the end tip of the microscope. The design of the cylindrical lenses at the tip of the optical end effector take into account the need to coincide the remote center of motion of the robot kinematics with the end vertex of the cylindrical lens.

In the illustrative embodiment, the overall body of the robot has been "biased" to a slant of 45 degrees. As a consequence, the bulk of the robotic system that is directly above the sample is reduced. This reduces the potential for collision with other robotic arms of the imaging system. But, as previously indicated, excitation light must remain coaxially aligned with the robotic arm, including at the optical end effector without regard to robotic motion. This is achieved via the use of a special prism known as a "half-pentaprism". Furthermore, the half pentaprism reduces the bulk of the robotic arm; its presence enables one elbow to be omitted from the robotic arm while maintaining the same maneuvering ability. As previously discussed, all elements of the optical end effector are "miniaturized" to take best advantage of the robotic arms.

An additional consideration in two-photon laser-scanning microscopy is a need to control the polarization state of the laser light that is delivered to the sample. This presents a potential problem in the context of embodiments of the present invention, wherein the joints consist of mirror pairs in periscope configuration. Specifically, when linearly polarized light reflects off of any real (i.e., commonly available) mirrors at an arbitrary angle, the reflected light does not necessarily remain linearly polarized. In fact, since the orientation of the mirrors change as the robotic arm assumes different configurations, the excitation light that exits the optical end effector should be considered to be arbitrarily polarized.

In some embodiments of the invention, the polarization problem is overcome through the use of specialized mirror coatings that ensure that linear polarization is maintained in reflection. In some embodiments, such linear polarization-maintaining mirrors are used throughout the free-space optics system within the robotic arms (with a single compensatory element to control the axis of polarization in the output light) to control the polarization state of the laser light, regardless of changes in the robot configuration. Linear polarization of light and its orientation relative to an internal robot frame-of-reference or an external laboratory frame-of-reference is maintained as the system orientation changes due to robot manipulation.

Some embodiments of the invention provide a robotic imaging system comprising a robotic imaging arm, wherein the robotic imaging arm includes (a) a first robotic arm having two rotational degrees of freedom and (b) a first free-space optical subsystem disposed in the first robotic arm, wherein the first free-space optical subsystem is configured to convey a first light signal through the first robotic arm to a first optical end effector at a distal end thereof, and wherein elements of the first free-space optical system maintain polarization of the first light signal while being conveyed through the first robotic arm.

BRIEF DESCRIPTION OF THE DRAWINGS

FIG. 4 depicts a schematic drawing of an objective of the optical subsystem of FIG. 3.

FIG. 5 depicts a ray trace of the propagation of light through a half pentaprism of the objective of FIG. 4.

DETAILED DESCRIPTION

Figure 1:
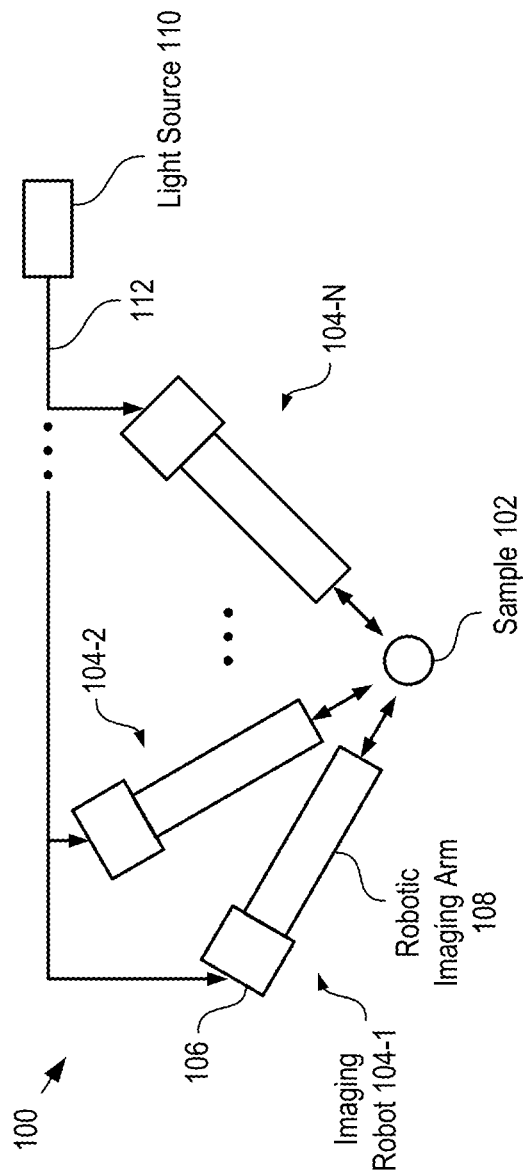
FIG. 1 depicts a portion of a robotic imaging system in accordance with an illustrative embodiment of the present invention.

FIG. 1 depicts a schematic drawing of a portion of an imaging system in accordance with an illustrative embodiment of the present invention. Robotic microscopy imaging system (hereinafter simply "imaging system") 100 is a laser-scanning microscopy system that comprises imaging robots 104-$i$, i=1, N (collectively "imaging robots 104") and light source 110. The number, N, of imaging robots 104 included in system 100 can be any practical number greater than one. In some other embodiments, the imaging system comprises a single imaging robot. Imaging system 100 can be used for conducting single-photon, two-photon, or, more generally, multi-photon microscopy.

Each of imaging robots 104 includes base 106 and robotic imaging arm 108. In some embodiments, imaging robots 104 are arranged in a fixed arrangement about sample 102.

Base 106 is a mechanically stable, fixed-position support for robotic imaging arm 108. Base 106 also includes optical elements for receiving free-space light from light source 110 and conveying the free-space light to robotic imaging arm 108. In some embodiments, base 106 is movable.

In some embodiments, base 106 includes telescoping linkages that provide it with positioning capability that enables reconfiguration of the arrangement of robots 104 around sample 102. This system configurability can reduce the likelihood of collision between multiple robots during their interaction with the sample. In some embodiments, base 106 is characterized by three translational degrees-of-freedom.

Robotic imaging arm 108 comprises a microscope system integrated with robot arm such that the objective of the microscope system can be positioned and oriented anywhere within a three-dimensional volume about sample 102. Robotic imaging arms 108 collectively enable simultaneous high-resolution imaging of different regions of sample 102. A representative imaging arm is described below and with respect to FIGS. 2-7.

Light source 110 is a conventional laser source operative for providing light signal 112 to each of imaging robots 104. An exemplary light source 110 is a Ti:Sapphire laser whose center wavelength is tunable within the range of approximately 700 nm to approximately 1000 nm. It will be clear to one skilled in the art, after reading this Specification, how to specify, make, and use systems comprising a different light source.

Light source 110 is optically coupled with each base 106 via a fixed free-space optical distribution system, which affords some key advantages, particularly for two-photon imaging embodiments. Specifically, it enables the excitation light delivered to sample 102 to have an arbitrarily wide spectral width. Because different biological fluorescent markers respond to different excitation wavelengths, using a free-space optical system to convey excitation light signal 112 to sample 102 enables the use of a broad pallet of biological fluorescent markers. In contrast, currently available optical fibers would limit system 100 to as few as one excitation wavelength and, therefore, one specific biomarker.

In some embodiments, light source 110 is optically coupled with each base 106 via optical fiber. While such an arrangement potentially provides system 100 with improved flexibility in position the robot bases about sample 102 (and, hence, higher potential packing density of microscopes in the sample region), the spectral bandwidth of an optical fiber-based distribution system can limit the types of fluorophores used—particularly for two-photon laser scanning microscopy. This limitation arises due to dispersion in a conventional optical fiber, which can cause femtosecond laser pulses to broaden in time. This can result in a significant reduction of the two-photon effect. In some embodiments, light source 110 and base 106 are optically coupled via optical fibers designed for conveying ultrashort pulses. But such fibers normally have a spectral bandwidth of only a few nanometers. As a consequence, such systems are typically limited to one fluorophore.

In some embodiments, base 106 and source 110 are dimensioned and arranged to enable changing the optical fiber used to couple them, which enables the use of a different wavelength of light.

In fiber-coupled systems, light source 110 will preferably include dispersion compensation elements and one or more fiber splitters, so that each imaging robot 104 receives a dispersion-compensated portion of light signal 112.

Figure 2:
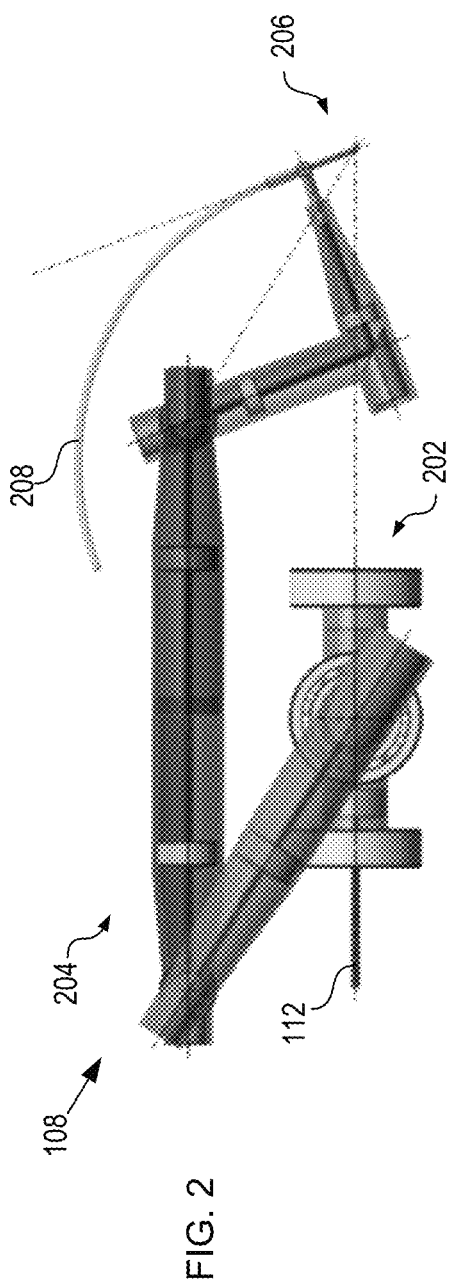
FIG. 2 depicts a representative robotic imaging arm in accordance with the illustrative embodiment of the present invention.

FIG. 2 depicts a schematic drawing of representative robotic imaging arm 108 in accordance with the illustrative embodiment of the present invention. Imaging arm 108 comprises robotic arm 202, optical system 204, objective 206, and collector 208.

Robotic arm 202 is a conventional articulated robot arm that is suitable for inclusion of optical elements within and/or attached to its links. Robotic arm 202 has two rotational degrees-of-freedom (with three translational degrees-of-freedom provided by base 106), which enables objective 206 to access any point of a three-dimensional space about sample 102 along any arbitrary direction. As a result, each robotic arm 202 can position its objective (i.e., part of the "optical end effector) in a manner to avoid mechanical and optical collision between all other objectives, as well as provide independent access to any location in sample 102 along its axis.

Robotic arm 202 employs kinematics known as "remote center of motion" ("RCM") in which its end effector (i.e., objective 206) pivots about a remote point; that is, away from mechanical bulk of the robotic arm. An RCM design facilitates accessing a small sample space (e.g., a mouse brain, etc.) with multiple objectives.

In some embodiments, the overall body of robotic arm 202 has been "biased" to a slant of 45°. This relocates the bulk of the robotic arm to a position that is not directly above sample 102, thereby reducing the potential for collision with other robotic arms of imaging system 100. Optically, this 45° biasing is enabled through use of a special prism known as a "half-pentaprism," as discussed below and with respect to FIG. 4. In some embodiments, the body of robotic arm 202 is biased at another angle via a prism or mirror configuration characterized by an angle other than 45°.

Optical system 204 is a free-space optical system that conveys excitation light from a suitable excitation laser source to objective 206. Optical system 204 is integrated with robotic arm 202 such that a mirror within the rotation joints rotates the laser (beam) spots at any angle without perturbing the optical alignment of the microscope.

Figure 3:
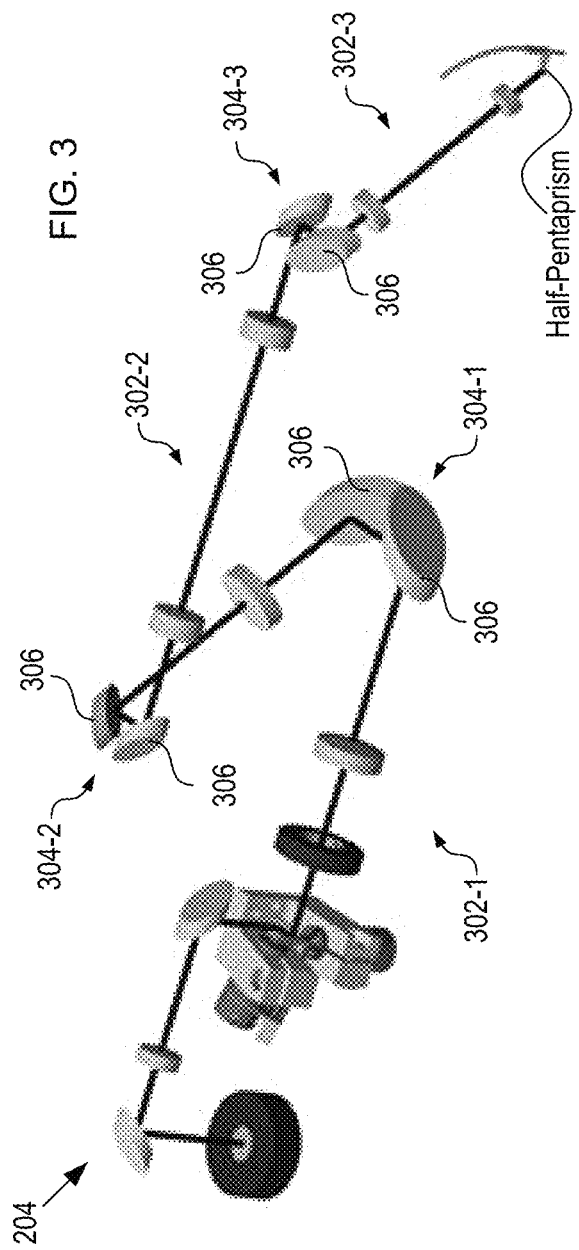
FIG. 3 depicts a schematic drawing of a free-space optical subsystem that is disposed in the robotic imaging arm of FIG. 2.

FIG. 3 depicts a schematic drawing of an optical system in accordance with the illustrative embodiment of the present invention. Optical system 204 comprises path segments 302-1 through 302-3 and joint systems 304-1 through 304-3.

Each of path segments 302-1 through 302-3 (referred to collectively as path segments 302) is a straight line optical path that is contained within a different link of robotic arm 202.

Each of joint systems 304-1 through 304-3 (referred to, collectively, as joint systems 304) comprises a pair of mirrors 306 that are arranged in a "periscope configuration," which enables light signal 112 to be optically coupled between two path segments without significant optical misalignment—even as the relative orientation of the path segments changes with the motion of robotic arm 204.

Path segments 302 and joint systems 304 collectively define an optical path that is co-aligned with the "skeleton" of robotic arm 202. This imbues optical system 204 with the same multiple degrees of freedom as that of the robotic arm.

One skilled in the art will recognize that the polarization state of the laser light that is delivered to the biological sample must typically be carefully controlled in two-photon laser-scanning microscopy. When linearly polarized light reflects off of a reflective element, the light can lose its linear polarization. Furthermore, when the incidence angle of the light on the reflective element changes, the polarization of the light changes as well.

In the illustrative embodiment, the reflective elements in joint systems 304 change their relative orientation with motion of robotic arm 202. As a result, light signal 112 can become arbitrarily polarized. In accordance with embodiments of the invention, in order to provide polarization control, each of mirrors 306 comprises a coating that preserves the linear polarization of light signal 112 as it propagates through optical system 204. In some embodiments, a compensatory element is also included to control the axis of polarization in the output excitation light.

Objective 206, also referred to herein as an "optical end effector," is a microscope objective suitable for illuminating an area of sample 102 with excitation light and for collecting light stimulated from the area. Objective 206 is characterized by an optical axis that is common to both the excitation light and the stimulated light. In addition, an importantly, objective 206 is miniaturized such that multiple objectives can be densely packed about sample 102. Sufficiently miniaturizing objective 206 enables simultaneous imaging of multiple regions of sample 102, which is precluded for prior art microscopes due to their bulk.

Miniaturization of objective 206 affords further advantages over prior-art brain imaging systems, such as fMRI. In particular, few if any of these prior-art techniques enable access to the complete brain at cellular resolution or over regions of more than a few cells at a time. In contrast, embodiments of the present invention enable recordation of hundreds of cells per imaged area, with imaged areas distributed over the brain.

FIG. 4 depicts a schematic drawing of an objective in accordance with the illustrative embodiment of the present invention. Objective 206 comprises lens 402, dichroic cube 407, lens 403, half pentaprism 404, and lens 410.

Lens 402 is a doublet lens whose design incorporates lens tip 408, which coincides with the remote center of motion of robotic arm 202. In other words, lens tip 408 remains aligned with the robotic axis 406, enabling robotic arm 202 to pivot about lens tip 408. In some embodiments, lens 402 is a doublet having a sample-side numerical aperture of approximately 0.50.

FIG. 5 depicts a ray tracing through half pentaprism 404. Referring to now to FIG. 5 and with continuing reference to FIG. 4, half pentaprism 404 is an optical element comprising surfaces 502 and 504, which collectively enable co-alignment of robot axis 406 and lens tip 408. Half pentaprism 404 redirects light signal 112 by 45°, such that robot axis 406 coincides with the sample-side tip of lens 402 (i.e., lens tip 408). In some embodiments, half pentaprism comprises high-index glass that has a refractive index of approximately 1.6. In some other embodiments, half pentaprism 404 comprises a different high-index glass.

Surface 502 enables light signal 112 to initially pass through by virtue of the incidence angle of the incoming light. Surface 504 reflects light signal 112 such that it is incident a second time on surface 502. However, this second incidence is at an angle that satisfies the total internal reflection condition for the type of glass used for pentaprism 404. As a result, surface 504 reflects substantially all of light signal 112 to mirror 506.

Mirror 506 comprises a dichroic mirror coating that is substantially completely reflective for the wavelengths of light signal 112, but substantially transparent for the fluorescence wavelengths of the fluorophores used to analyze sample 102. Mirror 506 reflects light signal 112 at an angle suitable to align it with the optical axis of lens 402. In some embodiments, half pentaprism has a field-of-view of approximately ±10° and is substantially diffraction limited over this field-of-view.

Lens 410 is a conventional graded-index (GRIN) fiber lens. In some embodiments, lens 410 is a cylindrical lens other than a GRIN lens.

By comparing FIG. 2 (half pentaprism not included) to FIG. 3 (half pentaprism included), those skilled in the art will appreciate that the presence of half pentaprism 404 enables the final elbow of the robotic arm (FIG. 2) to be omitted. (Three "elbows" [304-1, 304-2, and 304-3] are present in FIG. 3 while four elbows appear in FIG. 2.) This permits a significant reduction in the bulk of the robotic imaging system in the vicinity of a sample (without moving this bulk directly above the sample), thereby reducing the likelihood that multiple robotic imaging arms would collide with one another and the sample under investigation when used to simultaneously image multiple regions of a sample.

Figure 6A:
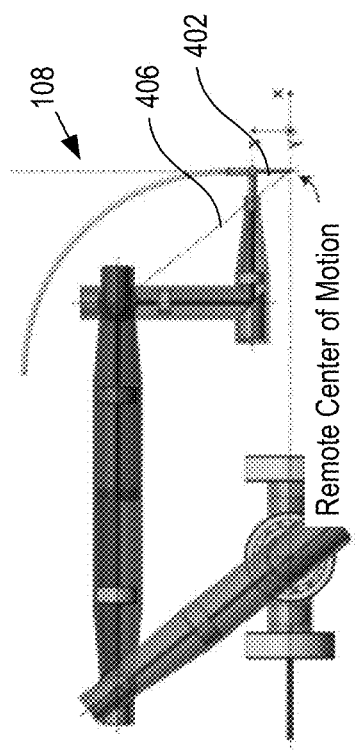
FIGS. 6A-C demonstrate co-alignment of the robotic axis, the optical axis, and lens tip, for a robotic imaging arm at three different tip positions.
Figure 6B:
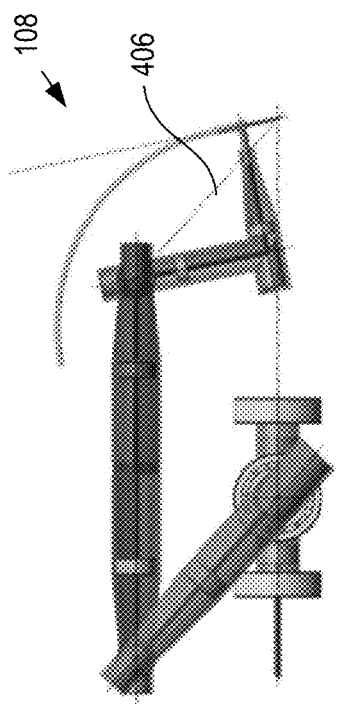
Figure 6C:
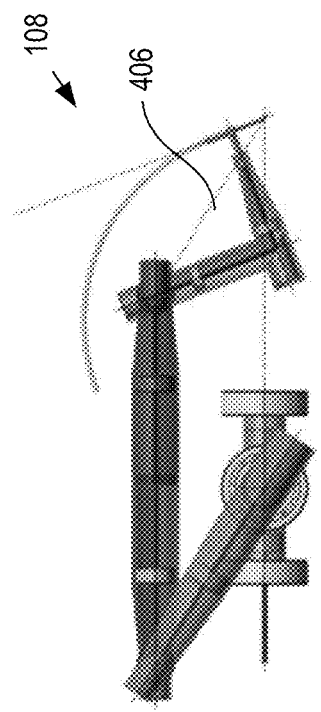

FIGS. 6A-C demonstrate the co-alignments of robotic axis 406, the optical axis of optical system 204, and lens tip 408, for robotic imaging arm 108 at three different tip positions. By enabling these co-alignments, the probability of inter-robot collisions and collisions with sample 102 during movement and static positioning is reduced. In these Figures, the robotic imaging arm does not include a half pentaprism, so an extra elbow is present (as previously discussed). Co-alignment of robotic axis 406, the optical axis of optical system 204, and lens tip 408 is also achieved, in accordance with the present teachings, when the robotic imaging arm includes the half pentaprism.

Figure 7:
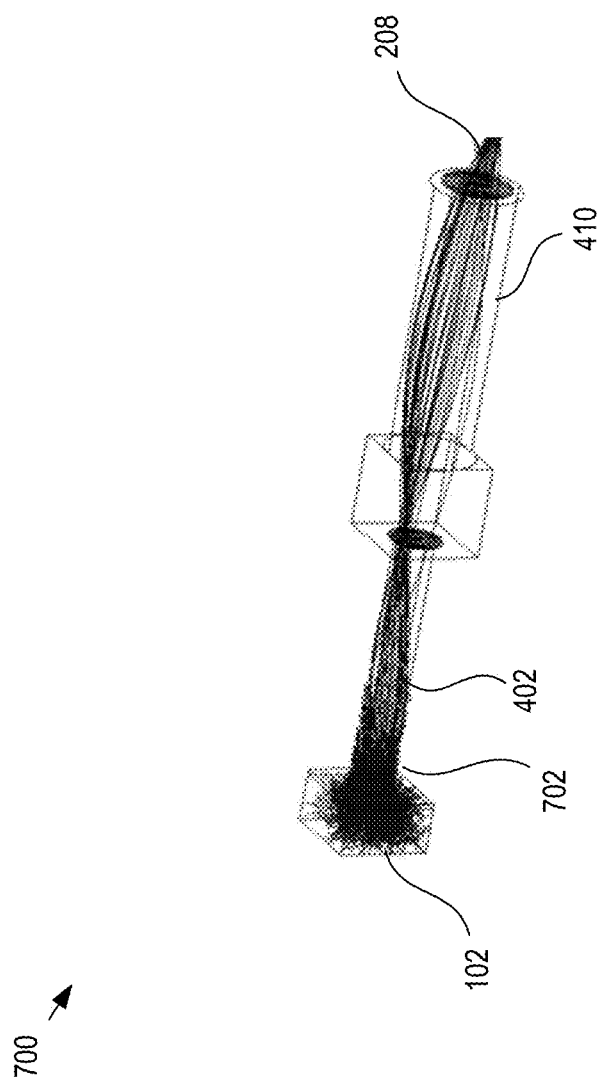
FIG. 7 depicts a ray trace, through the objective, for light from a sample.

FIG. 7 depicts a ray trace for light from sample 102 as it is collected by the optical end effector. Fluorophores located at sample 102 provide light signal 702, which includes fluorescent light at wavelengths dictated by the specific types of fluorophores used. In typical 2-photon imaging, the fluorescent wavelengths emitted by the fluorophores are shorter than those of light signal 112.

Light signal 702 is collected by lens 402, which then provides the light signal to lens 410 through dichroic mirror 506. Lens 410 then couples light signal 702 into collector 208. In the illustrative embodiment, collector 208 is a multimode optical fiber suitable for capturing a fluorescence signal from sample 102. In some embodiments, collector 208 is a plastic fiber to provide additional flexibility relative to a glass optical fiber. Even though propagation loss in a plastic optical fiber is somewhat higher than for that of a glass fiber, for fiber lengths of about 1 meter, greater than 95% of the captured light is transmitted through the plastic fiber. The spectral bandwidth of a typical multimode fiber is wide enough so that it does not limit collection of fluorescence signals from a large number of fluorophores.

Collector 208 conveys the fluorescent light from sample 102 to suitable photodetectors (not shown).

The size of the optical end effector—objective 206—substantially dictates the number of robotic imaging arms that can be used to analyze of a given sample. In some embodiments, the elements of objective 206 are miniaturized to a very small size; that is, less than about 13 millimeters, preferably less than about 6 millimeters, more preferably less than about 3 millimeters, and most preferably about 1 millimeter or less in diameter, to enable the simultaneous use of many robotic imaging arms on a small sample, such as a mouse brain.

In the illustrative embodiment, the source of excitation light couples to the robotic imaging arms via free-space optics. In some alternative embodiments, the light source is coupled to the robotic arms via guided-wave optics (e.g., optical fiber, etc.).

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A robotic imaging system comprising:
    a first robotic imaging arm including:
    (a) a first robotic arm having two rotational degrees of freedom; and
    (b) a first free-space optical subsystem disposed in the first robotic arm, wherein the first free-space optical subsystem is configured to convey a first light signal through the first robotic arm to a first optical end effector at a distal end thereof, and wherein elements of the first free-space optical system maintain polarization of the first light signal while being conveyed through the first robotic arm.

2. The robotic imaging system of claim 1, wherein the first robotic arm has a first robotic axis, and wherein the first optical end effector has a first objective tip, and further wherein the first objective tip is aligned with the first robotic axis.

3. The robotic imaging system of claim 2, wherein the first optical end effector further includes a half pentaprism.

4. The robotic imaging system of claim 2, wherein the first robotic arm is characterized by kinematics that defines a remote center of motion that is coincident with the first objective tip.

5. The robotic imaging system of claim 1, wherein the first free-space optical subsystem is operative for two-photon imaging.

6. The robotic imaging system of claim 1, further comprising a second robotic imaging arm, wherein the second robotic imaging arm includes:
    (a) a second robotic arm having two rotational degrees of freedom; and
    (b) a second free-space optical subsystem disposed in the second robotic arm, wherein the second free-space optical subsystem is configured to convey a second light signal through the second robotic arm to a second optical end effector at a distal end thereof, and further wherein elements of the second free-space optical system maintain polarization of the second light signal while being conveyed through the second robotic arm.

7. The robotic imaging system of claim 6 wherein the first light signal has a first wavelength and the second light signal has a second wavelength and wherein the first wavelength and the second wavelength are different from one another.

8. The robotic imaging system of claim 6 wherein:
    (a) the first robotic arm is characterized by a first field-of-view and the second robotic arm is characterized by a second field-of-view;
    (b) the first optical end effector conveys the first light signal to a first location on a three-dimensional sample and the second optical end effector conveys the second light signal to a second location on the three-dimensional sample; and
    (c) the first location is outside the second field-of-view and the second location is outside the first field-of-view.

9. The robotic imaging system of claim 1 wherein the first optical end effector conveys the first light signal to a first location on a three-dimensional sample and receives light from the first location and couples it into a first collector.

10. The robotic imaging system of claim 1 wherein the first free-space optical system includes a first mirror pair, wherein the first mirror pair is disposed at a first rotary joint of the first robotic arm, wherein the first mirror pair is arranged in a periscope configuration.

11. The robotic imaging system of claim 1 further comprising a light source that provides the first light signal, wherein the light source is optically coupled to the first robotic imaging arm via free-space optics or guided wave optics.

12. The robotic imaging system of claim 1 further comprising a first optical implant for implanting into a three-dimensional sample, wherein the first robotic imaging arm is operative to interrogate the first optical implant.

13. A robotic imaging system comprising:
    a plurality of robotic imaging arms, wherein each robotic imaging arm includes a robotic arm and a free-space optical subsystem that is located therein, wherein the free-space optical system conveys an excitation light signal from a proximal end of the robotic arm to an objective at a distal end of the robotic arm; and
    a light source that provides the light signal, wherein the light signal comprises a plurality of wavelengths, and wherein the light source is optically coupled to the free-space optical subsystem in each of the robotic imaging arms.

14. The robotic imaging system of claim 13 wherein each robotic arm has at least one characteristic selected from the group consisting of: at least two rotational degrees-of-freedom and kinematics that define a remote center of motion that is coincident with an objective tip included in the objective.

15. The robotic imaging system of claim 13 wherein each robotic arm provides at least two rotational degrees-of-freedom, is characterized by remote center-of-motion kinematics, and has an objective having a diameter of about 6 millimeters or less.

16. The robotic imaging system of claim 15 wherein the plurality of robotic imaging arms are positioned for simultaneous imaging of a plurality of locations within a sample, and wherein each of the plurality of robotic imaging arms is characterized by a first field-of-view, and further wherein the plurality of locations are located in an area that is larger than the first field-of-view.

17. The robotic imaging system of claim 13 wherein the free-space optical subsystem of each robotic imaging arm maintains linear polarization of the light signal conveyed therethrough.

18. The robotic imaging system of claim 13 wherein the free-space optical subsystem of each robotic imaging arm includes a mirror pair that is located at a rotary joint of each robotic imaging arm, wherein the mirror pair is arranged in a periscope configuration.

19. The robotic imaging system of claim 13 wherein the objective in each free-space optical subsystem comprises a half pentaprism and a dichroic mirror.

20. The robotic imaging system of claim 18 wherein the dichroic mirror is arranged to couple light, which is received from a three-dimensional sample that has been illuminated by the first signal, into a multimode optical fiber.

* * * * *